United States Patent [19]

Vannice

[11]  4,041,087
[45]  Aug. 9, 1977

[54] METHOD FOR THE DIRECT PREPARATION OF HALOGENATED HYDROCARBONS BY THE REACTION OF CO, H$_2$ AND HALOGEN IN THE PRESENCE OF A CATALYST

[75] Inventor: M. Albert Vannice, Boalsburg, Pa.

[73] Assignee: Exxon Research and Engineering Company, Linden, N.J.

[21] Appl. No.: 607,763

[22] Filed: Aug. 26, 1975

[51] Int. Cl.$^2$ .................. C07C 19/00; C07C 27/06
[52] U.S. Cl. .................. 260/652 R; 260/449 R; 260/449 M; 260/653; 260/664
[58] Field of Search .................. 260/652 R, 653, 664, 260/449 R, 449 M

[56] References Cited

U.S. PATENT DOCUMENTS 3,182,092  5/1965  Haszeldine et al. .................. 260/653

FOREIGN PATENT DOCUMENTS 1,215,618  5/1966  Germany .................. 260/652 R Primary Examiner—C. Davis
Attorney, Agent, or Firm—Joseph J. Allocca; E. A. Forzano

[57]  ABSTRACT

Halogenated hydrocarbons are selectively prepared under mild reaction conditions by flowing a gaseous mixture of H$_2$, CO, and halogen selected from the group consisting of chlorine, bromine and iodine over a well-dispersed supported catalyst system, such as Pt/Re, Pt/Ir, Pt, Ir and Re on an acidic support such as Al$_2$O$_3$, SiO$_2$-Al$_2$O$_3$ or zeolites. The reaction occurs over a broad temperature range of from 200° to 1,000° C and a pressure of from 0.1 to 500 atmospheres.

18 Claims, No Drawings

METHOD FOR THE DIRECT PREPARATION OF HALOGENATED HYDROCARBONS BY THE REACTION OF CO, H₂ AND HALOGEN IN THE PRESENCE OF A CATALYST

FIELD OF THE INVENTION

The instant invention relates to a method for preparing halogenated hydrocarbons of the formula $C_AH_{2A+2-B}X_B$ wherein X is a halogen selected from the group consisting of chlorine, bromine, iodine, and fluorine, A is an integer of from 1 to 4 inclusive, preferably 1 and 2, and B is an integer of from 1 to 10, except that $2A+2-B$ may not be less than zero; the method of preparation comprising directing a stream of synthesis gas comprising CO and $H_2$ over a well-dispersed supported metal catalyst, the metal catalyst being selected from the group consisting of Group VIII metals and rhenium, preferably Pt, Ir or Pt/Ir and Pt/Re alloys, and the support material being an acidic metal oxide such as $Al_2O_3$, $SiO_2$—$Al_2O_3$, etc., and introducing into the synthesis gas system before the catalyst, a stream of halogen, passing the mixed stream over the catalyst, heating the system to a temperature sufficient to facilitate reaction, for example, a temperature between 200° to 1000° C at a pressure sufficient to facilitate the reaction, for example, 0.1 to 500 atmospheres.

BACKGROUND OF THE INVENTION

Halogenated hydrocarbons as typified by methyl chloride have been produced in laboratory quantities since as early as the first half of the 19th Century. The reaction used consisted of heating crude methyl alcohol with a mixture of sulfuric acid and sodium chloride. Other early synthetic preparation reactions included reacting phosphorous chlorides with methyl alcohol while if pure methyl chloride was required, it could be prepared by passing hydrogen chloride into a boiling solution of zinc chloride slurried in twice its weight of methanol.

In 1875, methyl chloride in small laboratory or limited commercial quantities was prepared by the thermal decomposition of betaine $(CH_3)_3NCH_2C(O)O$, a waste byproduct of the best sugar industry.

Currently, there are two industrial methods for preparing methyl chloride, namely, chlorination of methane and reaction of hydrogen chloride with methanol. Chlorination of methanol yields methyl chloride as the sole product, but chlorination of methane either thermally, photochemically or catalytically yields mixed products consisting of methyl chloride, methylene chloride, chloroform and carbon tetrachloride; all of which have commercial importance.

Methyl chloride is readily converted to the corresponding bromide or iodide by reacting it in hot acetone solution with a sodium halide salt.

It has been discovered and forms the basis of the disclosure, that halogenated hydrocarbons of the formula $C_AH_{2A+2-B}X_B$ wherein X is a halogen selected from the group consisting of fluorine, chlorine, bromine and iodine, A is an integer of from 1 to 4 inclusive, preferably 1 to 2, and B is an integer of from 1 to 10 inclusive, except that $2A+2-B$ may not be less than zero, can be produced directly under relatively mild reaction conditions by flowing a gaseous mixture of CO, $H_2$ and halogen in the form of any halogen-containing material that will exchange $X^-$ groups with $OH^-$ groups on an oxide surface, the preferred halogen source being $X_2$ and HX over a catalyst material which is in combination with an acidic inorganic oxide material. The reaction occurs over a wide range of temperatures, i.e., 200° to 1,000° C, preferably 200°–700° C, most preferably 250°–400° C and at pressures ranging from 0.1 to 500 atm., preferably 1–20 atm., most preferably 1–10 atm. The products which are produced by this reaction range from methyl halide, methylene halide, methyl haloform and carbon tetrahalide to halogenated ethane, propane and traces of butyl-halides. However, the predominant products are methyl halides, especially monohalomethane.

The catalyst material in combination with an acidic inorganic oxide medium which may be employed for the reaction may be either mixed with the acidic inorganic oxide or is preferably supported in a dispersed state on the acidic inorganic oxide medium. The catalyst material is selected from the group consisting of Group VIII and Re, preferably Pt, Ir, Re and combinations thereof (Pt/Ir, Pt/Re) while the support medium may be any convenient conventional acidic support material known in the art, for example, alumina, silica-alumina, zeolite, etc., the most preferred being alumina, and the most preferred catalyst-support combination being platinum on alumina. The catalyst material may be present at from 0.01 to 5.0 wt. % based on the acidic inorganic oxide medium (be the medium present as intimately mixed with the catalyst or as catalyst support) preferably, the catalyst material is present at from 0.1 to 2.0 wt. % based on the acidic inorganic oxide medium.

The catalyst may be prepared by any of the methods common to those skilled in the art, one typically being impregnation of the support with chloroplatinic acid followed by drying, calcining and reduction by methods known in the art.

By careful selection of a metal catalyst which possesses selectivity for the preparation of one type of hydrocarbon (for example, $Pt/Al_2O_3$, which is selective to methane) $C_1$ halides can be produced and this selectivity can be encountered and advantageously exploited at temperatures lower than those normally utilized by the prior art wherein no catalyst was employed. However, a major advantage over the current methods of synthesis is the fact that the instant invention eliminates the need for utilizing intermediate chemicals such as $CH_4$ or methanol, that is, the instant invention is a direct one-step synthesis, whereas the prior art must initially prepare a stable intermediary material which is subsequently converted into halohydrocarbons. With the increasing availability of synthesis gas (CO and $H_2$) from the expanding use of gasification processes, the instant invention of direct synthesis is highly desirable, economical and, with the availability of selectivity of product composition by judicious selection of catalyst and because of the lower temperature of reaction, the preferable route.

The materials utilized, CO, $H_2$ and halogen source, are mixed so as to achieve an $H_2/CO/X$ ratio of 0.5–10/1/0.1–10, preferably a ratio of 1–4/1/0.5–2 being utilized. The materials may be mixed in any order.

Chloride has been shown to poison typical Fischer-Tropsch catalysts such as precipitated Fe-Cu catalysts (see for example, Hofer, L. J. E, Anderson, R. B., Peebles, W. C. and Stein, K. C., J. Phys. Colloid Chem. 55, 1201 (1951)). However, if a metal is chosen that is not susceptible to chloride poisoning and is selective in the type of hydrocarbons produced, it is possible to selectively produce specific chlorinated hydrocarbons. Pt fulfills these requirements (when utilizing chlorine especially) since:

a. it is known to be an active hydrogenation catalyst in the presence of Cl⁻, i.e., it is used as a reforming catalyst, b. Pt has been shown to be a selective catalyst for the production of methane, and c. by dispersing Pt on the appropriate support not only is the activity increased, but the presence of hydroxyl groups on the oxide support allows an exchange to occur between $Cl_2$ gas or Cl⁻ ions (HCl) to produce Cl⁻ ions on the support surface. This facilitates the formation of chlorinated hydrocarbons. Any such metal oxide support capable of this exchange reaction will work; however, high surface area acidic $Al_2O_3$ is particularly desirable.

Reaction conditions, in general, include the range where methane is selectively produced, i.e. 200°–1000° C and 1–500 atm. In particular, a preferred range is 250°–350° C and 1–10 atm. pressure using a $Pt/Al_2O_3$ catalyst.

EXAMPLE 1

Chloride was placed on a Pt catalyst by impregnating $\eta$-$Al_2O_3$ with chloroplatinic acid ($H_2PtCl_6$) by a typical aqueous impregnation technique. A 1.75 wt.% Pt/$Al_2O_3$ catalyst was prepared in this manner which contained 1.9 wt. % chlorine on the surface of the $Al_2O_3$. A 0.49 g sample was placed in a glass reactor. After a 1 hour reduction in flowing $H_2$ at 450° C, the temperature was reduced to 272° C and a gas mixture containing a $H_2/CO$ mole ratio of 1.2 was flowed through the catalyst bed at 1 atm. pressure. The product gases consisted of 48 mole % $CH_4$, 7 mole % $C_2H_6$, 1 mole % $C_2H_4$, and 44 mole % $CH_3Cl$. As the amount of Cl remaining on the surface continually was depleted, the amount of $CH_3Cl$ being formed was reduced. Chlorine in the form of chloride ions is therefore shown to be incorporated into the hydrocarbon intermediate species present during the synthesis reaction.

EXAMPLE 2

A sample of 0.6% Pt/$\gamma$-$Al_2O_3$ catalyst was sieved and 2.8 g of the 10/20 mesh cut were placed in an autoclave reactor. The sample was reduced for 16 hours at 200° C under an $H_2$ flow of 140 cc/min. The catalyst was then heated to 325° C and reduced at this temperature for 1 hour under the same $H_2$ flow. The autoclave was cooled to room temperature, 0.20 atm. of $Cl_2$ was added, then 0.41 atm. of CO was added to the original $H_2$ pressure of 1 atm giving a final total pressure of 1.6 atm. with an initial $H_2$:CO:$Cl_2$ mole ratio of 5:2:1. The autoclave was then heated to the reaction temperature of 280° C.

The reaction proceeded for 16 hours during which time 19% of the initial CO fraction had been reacted to organic compounds. A mass spectrometric analysis of gas products gave the following analysis, shown in Table I.

EXAMPLE 3

A sample of pre-reduced 1.75% Pt/$\eta$-$Al_2O_3$ was placed in an autoclave and purged with Ar. The sample weight was 0.984 g catalyst. To 1 atm. Ar pressure in the autoclave at room temperature were added in the following order: 1.7 atm. $H_2$, 1.4 atm. of a $H_2$/CO mixture containing 48.4% $H_2$ and 51.6% CO, and finally 1.0 atm. of HCl giving a final total pressure of 5.1 atm. and an initial $H_2$/CO/HCl mole ratio of 3.4:1:1.4. The diluent Ar is not necessary but was used as a flush gas. The autoclave was then heated to 270° C. After one-half hour at this temperature, 10.6% of the original CO content had been reacted. Analysis by gas chromatography gave the results listed in Table II. This verifies that addition of chloride in the form of HCl to a CO/$H_2$ mixture results in a very selective process forming methyl chloride.

TABLE I

| Compound | Residual Gas Analysis Mole % | Product Mole % |
|---|---|---|
| $H_2$ | 69.7 | |
| HCl | 3.7 | |
| CO | 10.3 | |
| $CO_2$ | 9.7 | |
| Air | 2.3 | |
| $H_2O$ | 1.6 | |
| $CH_4$ | 0.4 | 15 |
| $C_2H_6$ | 0.3 | 11 |
| $C_3$ | 0.2 | 7 |
| $CH_3Cl$ | 0.6 | 22 |
| $C_2H_5Cl$ | 1.2 | 44 |

Here it is demonstrated that the addition of gaseous $Cl_2$ to a CO + $H_2$ mixture produces large quantities of methyl chloride and ethyl chloride.

TABLE II

| Compound | Residual Gas Analysis Mole % | Product Mole % |
|---|---|---|
| Ar | 18.0 | |
| $N_2$ | 56.7 | |
| CO | 21.6 | |
| $CH_4$ | 0.11 | 4.3 |
| $CO_2$ | 0.18 | |
| $C_2H_4$ | 0.01 | 0.3 |
| $C_2H_6$ | 0.03 | 1.2 |
| $H_2O$ | 1.00 | |
| $CH_3Cl$ | 2.40 | 94.2 |

$H_2$ & HCl — not determined.

What is claimed is:

1. A method for the preparation of halogenated hydrocarbons of the formula $C_AH_{2A+2-B}X_B$ wherein X is a halogen selected from the group consisting of fluorine, chlorine, bromine and iodine, A is an integer ranging from 1 to 4 inclusive and B is an integer ranging from 1 to 10 inclusive, except that 2A+2−B may not be less than zero, which method comprises the steps of:
   1. preparing a system comprising CO, $H_2$ and a source of halogen wherein the source of halogen is selected from the group consisting of molecular halogen and hydrogen halides;
   2. passing said system over a catalyst metal selected from the group consisting of Group VIII metals, rhenium, and platinum-iridium and platinum-rhenium alloys, which catalyst metal is in combination with an acidic inorganic oxide material;
   3. heating the system containing the CO, $H_2$ and halogen source over the catalyst to a temperature in the range of 200° C – 1000° C; and
   4. pressurizing the system to a level in the range of 0.1 atm. to 500 atm.

2. The process of claim 1 wherein the source of halogen is selected from the group consisting of molecular chlorine, molecular bromine, hydrogen chloride and hydrogen bromide.

3. The process of claim 1 wherein the source of halogen is selected from the group consisting of molecular chlorine and hydrogen chloride.

4. The method of claim 1 wherein the catalyst metal is selected from the group consisting of Group VIII metals and rhenium.

5. The method of claim 1 wherein the catalyst metal is selected from the group consisting of platinum, iridium, rhenium, platinum-iridium and platinum-rhenium alloys.

6. The method of claim 1 wherein the catalyst metal is supported on the acidic inorganic oxide material.

7. The method of claim 6 wherein the support material is selected from the group consisting of alumina, silica-alumina and zeolite.

8. The method of claim 7 wherein the support material is alumina.

9. The method of claim 1 wherein the catalyst metal is present at from 0.01 to 5.0 wt. %.

10. The method of claim 1 wherein the catalyst metal is present at from 0.1 to 2.0 wt. %.

11. The method of claim 1 wherein the temperature of reaction is betweem 250° to 400° C.

12. The method of claim 1 wherein the pressure of reaction is between 1 to 20 atmospheres.

13. The method of claim 1 wherein the gas comprises a mixture of $H_2$, CO and halogen source present in the ratio of 0.5–10 : 1 : 0.1–10.

14. The method of claim 1 wherein the gas comprises a mixture of $H_2$, CO and halogen source preferably present in a ratio of 1–4 : 1 : 0.5–2.

15. The method of claim 1 wherein X is chlorine, A is 1 or 2, B is 1, wherein the supported catalyst is platinum on alumina, the temperature is between 250° to 350° C, the pressure is from 1 to 10 atmospheres and the halogen source is selected from the group consisting of molecular chlorine and hydrogen chloride.

16. The method of claim 15 wherein the gas comprises a mixture of $H_2$, CO and chlorine present in a ratio of 5:2:1.

17. The method of claim 15 wherein the gas comprises a mixture of $H_2$, CO and HCl present in a ratio of 3.4 : 1 : 1.4.

18. The method in claim 1 wherein the catalyst metal is selected from the group consisting of platinum, iridium and rhenium.

* * * * *